US012403174B2

(12) United States Patent
Wang et al.

(10) Patent No.: US 12,403,174 B2
(45) Date of Patent: Sep. 2, 2025

(54) IMMUNOMODULATORS

(71) Applicant: Bristol-Myers Squibb Company, Princeton, NJ (US)

(72) Inventors: Tao Wang, Farmington, CT (US); Paul Michael Scola, Glastonbury, CT (US); Zhongxing Zhang, Madison, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 680 days.

(21) Appl. No.: 17/791,027

(22) PCT Filed: Nov. 19, 2020

(86) PCT No.: PCT/US2020/061273
§ 371 (c)(1),
(2) Date: Jul. 6, 2022

(87) PCT Pub. No.: WO2021/141684
PCT Pub. Date: Jul. 15, 2021

(65) Prior Publication Data
US 2023/0065827 A1   Mar. 2, 2023

Related U.S. Application Data

(60) Provisional application No. 62/957,383, filed on Jan. 6, 2020.

(51) Int. Cl.
*A61K 38/12*  (2006.01)
*A61P 37/04*  (2006.01)

(52) U.S. Cl.
CPC .............. *A61K 38/12* (2013.01); *A61P 37/04* (2018.01)

(58) Field of Classification Search
None
See application file for complete search history.

(56) References Cited

U.S. PATENT DOCUMENTS

| | | | |
|---|---|---|---|
| 5,869,451 A | 2/1999 | Dower et al. | |
| 9,090,668 B2 | 7/2015 | Suga et al. | |
| 9,308,236 B2 | 4/2016 | Miller et al. | |
| 9,410,148 B2 | 8/2016 | Suga et al. | |
| 9,732,119 B2 | 8/2017 | Sun et al. | |
| 9,809,625 B2 | 11/2017 | Boy et al. | |
| 9,850,283 B2 | 12/2017 | Miller et al. | |
| 9,856,292 B2 | 1/2018 | Gillman et al. | |
| 9,861,680 B2 | 1/2018 | Mapelli et al. | |
| 9,879,046 B2 | 1/2018 | Miller et al. | |
| 9,944,678 B2 | 4/2018 | Sun et al. | |
| 10,143,746 B2 | 12/2018 | Allen et al. | |
| 10,358,463 B2 | 7/2019 | Miller et al. | |
| 10,406,251 B2 | 9/2019 | Morin et al. | |
| 10,450,347 B2 | 10/2019 | Miller et al. | |
| 10,538,555 B2 | 1/2020 | Miller et al. | |
| 10,633,419 B2 | 4/2020 | Gillman et al. | |
| 10,988,507 B2 | 4/2021 | Gillman et al. | |
| 11,066,445 B2 | 7/2021 | Gillman et al. | |
| 11,103,605 B2 | 8/2021 | Donnelly et al. | |
| 11,358,988 B2 | 6/2022 | Gillman et al. | |
| 11,492,375 B2 | 11/2022 | Miller et al. | |
| 2010/0168380 A1 | 7/2010 | Suga et al. | |
| 2013/0178394 A1 | 7/2013 | Suga et al. | |
| 2014/0018257 A1 | 1/2014 | Suga et al. | |
| 2016/0222060 A1 | 8/2016 | Miller et al. | |
| 2017/0369530 A1 | 12/2017 | Miller et al. | |
| 2021/0386876 A1 | 12/2021 | Donnelly et al. | |
| 2022/0251141 A1 | 8/2022 | Wang et al. | |
| 2022/0389061 A1 | 12/2022 | Wang et al. | |
| 2023/0022400 A1 | 1/2023 | Wang et al. | |
| 2023/0063238 A1 | 3/2023 | Wang et al. | |
| 2023/0101323 A1 | 3/2023 | Gillman et al. | |

FOREIGN PATENT DOCUMENTS

| | | |
|---|---|---|
| WO | WO-200026353 A1 | 5/2000 |
| WO | WO-2007005874 A2 | 11/2007 |
| WO | WO-2010027828 A2 | 3/2010 |
| WO | WO-2011161699 A2 | 12/2011 |
| WO | WO-2012168944 A1 | 12/2012 |
| WO | WO-2013010573 A1 | 1/2013 |
| WO | WO-2013144704 A1 | 10/2013 |
| WO | WO-2013182240 A1 | 12/2013 |
| WO | WO-2013182662 A1 | 12/2013 |
| WO | WO-2013183707 A1 | 12/2013 |
| WO | WO-2014151006 A2 | 9/2014 |
| WO | WO-2014151634 A2 | 9/2014 |
| WO | WO-2015033303 A1 | 3/2015 |
| WO | WO-2015044900 A1 | 4/2015 |
| WO | WO-2016039749 A1 | 3/2016 |
| WO | WO-2016057624 A1 | 4/2016 |

(Continued)

OTHER PUBLICATIONS

Hayashi, Y., et al., "In Vitro Selection of Anti-Akt2 Thioether-Macrocyclic Peptides Leading to Isoform-Selective Inhibitors," ACS Chemical Biology 7(3):607-613, American Chemical Society, United States (Mar. 2012).

Morimoto, J., et al., "Discovery of Macrocyclic Peptides Armed with a Mechanism-Based Warhead: isoform-Selective Inhibition of Human Deacetylase SIRT2," Angewandte Chemie International Edition 51(14):3423-3427, Wiley-VCH, Germany (Apr. 2012).

Yamagishi, Y., et al., "Natural Product-Like Macrocyclic N-Methyl-Peptide Inhibitors Against a Ubiquitin Ligase Uncovered from a Ribosome-Expressed De Novo Library," Chemistry & Biology 18(12):1562-1570, Elsevier, United States (Dec. 2011).

Hoyer, K.M., et al., "The Iterative Gramicidin S Thioesterase Catalyzes Peptide Ligation and Cyclization," Chemistry & Biology 14(1):13-22, Elsevier, United States (Jan. 2007).

(Continued)

Primary Examiner — Noble E Jarrell

(57) ABSTRACT

In accordance with the present disclosure, macrocyclic compounds have been discovered that bind to PD-L1 and are capable of inhibiting the interaction of PD-L1 with PD-1 and CD80. These macrocyclic compounds exhibit in vitro immunomodulatory efficacy thus making them therapeutic candidates for the treatment of various diseases including cancer and infectious diseases.

13 Claims, No Drawings

(56) References Cited

FOREIGN PATENT DOCUMENTS

| WO | WO-2016077518 A1 | 5/2016 |
|---|---|---|
| WO | WO-2016086036 A2 | 6/2016 |
| WO | WO-2016100285 A1 | 6/2016 |
| WO | WO-2016100608 A1 | 6/2016 |
| WO | WO-2016126646 A1 | 8/2016 |
| WO | WO-2016149351 A1 | 9/2016 |
| WO | WO-2017151830 A1 | 9/2017 |
| WO | WO-2017176608 A1 | 10/2017 |
| WO | WO-2017201111 A1 | 11/2017 |
| WO | WO-2018085750 A2 | 5/2018 |
| WO | WO-2018237153 A1 | 12/2018 |
| WO | WO-2019070643 A1 | 4/2019 |
| WO | WO-2020237081 A1 | 11/2020 |

OTHER PUBLICATIONS

Karle, I. L., "Conformation of Cyclic Pentapeptides in the Crystalline State. Cyclic (D-Phe-L-Pro-Gly-D-Ala-L-Pro) with 3.fwdarw. 1 and 4.fwdarw. 1 Intramolecular Hydrogen Bonds", Database Accession No. 1981: 498291; Compound 78221-87-1.

Rothe, M., et al., "Interchain Reactions (Cyclo-Oligomerizations) During the Cyclization of Resin-Bound Peptides," Database Accession No. 1978: 424771; Compound RN: 66517-17-7.

Cook, J.W., et al., "Crystal Structure and Conformation of the Cyclic Trimer of a Repeat Pentapeptide of Elastin, cyclo-(L-valy1-L-prolylglycyl-L-valylglycyl)3," Journal of the American Chemical Society 102(17): 5502-5505, American Chemical Society, United States (Aug. 1980).

Tamaki, M., et al., "Cyclization of Penta- and Hexapeptide Active Esters Related to Gramicidin S and Gratisin," Bulletin of the Chemical Society of Japan 62(2):594-596, Chemical Society of Japan, Japan (Feb. 1989).

Maute, R., et al., "Engineering High-Affinity PD-1 Variants for Optimized Immunotherapy and Immune-PET Imaging," Proceedings of the National Academy of Sciences of the United States of America 112:E6506-E6514, National Academy of Sciences, United States (Nov. 2015).

Wang, F. et al., "Synthetic Small Peptides Acting on B7H1 Enhance Apoptosis in Pancreatic Cancer Cells", Molecular Medicine Reports 6: 553-557, Spandidos Publications, Greece (2012).

Nowak, M.W. et al., "In Vivo Incorporation of Unnatural Amino Acids into Ion Channels in Xenopus Oocyte Expression System." Methods Enzymol. ( 1988) 293 p. 504-529.

Zhong, W. et al., "From ab initio Quantum Mechanics to Molecular Neurobiology: a Cation-Pi Binding Site in the Nicotinic Receptor." PNAS (1998) 95 p. 12088-12093.

Zhang, R. et al., "Fluorescence Polarization Assay and Inhibitor Design for MDM2/p53 Interaction." Anal. Biochem. (2004) 331 p. 138-146.

Judd, A. K. et al., "Structure-Activity Studies on High Affinity NOP-Active Hexapeptides." J. Peptide. Res. (2004) 64(3) p. 87-94.

Noichl, B.P. et al., "Toward Intrinsically Colored Peptides: Synthesis and Investigation of the Spectral Properties of Methylated Azatryptophans in Tryptophan-Cage Mutants." Biopolymers (2015) 104 p. 585-600.

Dolusic, E. et al., "Tryptophan 2,3-Dioxygenase (TDO) Inhibitors. 3-(2-(Pyridyl)ethenyl)indoles as Potential Anticancer Immunomodulators." J. Med. Chem. (2011) 54 p. 5320-5334.

Matsuura, S.. et al., "Studies of peptide antibiotics XXVIII Synthesis of sesquigramicidin S and Digramicidin S," Bulletin of the Chemical Society of Japan 46(3): p. 977-985.

International Search Report and Written Opinion for International Application No. PCT/US2020/061273, European Patent Office, Netherlands, mailed Feb. 8, 2021, 14 pages.

IMMUNOMODULATORS

CROSS-REFERENCE TO RELATED APPLICATIONS

This PCT application claims the priority benefit of U.S. Provisional Application No. 62/957,383, filed Jan. 6, 2020 which is incorporated herein by reference in its entirety.

FIELD

The present disclosure provides macrocyclic compounds that bind to PD-L1 and are capable of inhibiting the interaction of PD-L1 with PD-1 and CD80. These macrocyclic compounds exhibit in vitro immunomodulatory efficacy thus making them therapeutic candidates for the treatment of various diseases including cancer and infectious diseases.

BACKGROUND

The protein Programmed Death 1 (PD-1) is an inhibitory member of the CD28 family of receptors, that also includes CD28, CTLA-4, ICOS and BTLA. PD-1 is expressed on activated B cells, T cells, and myeloid cells.

The PD-1 protein is a 55 kDa type I transmembrane protein that is part of the Ig gene superfamily. PD-1 contains a membrane proximal immunoreceptor tyrosine inhibitory motif (ITIM) and a membrane distal tyrosine-based switch motif. Although structurally similar to CTLA-4, PD-1 lacks the MYPPY motif that is critical for CD80 CD86 (B7-2) binding. Two ligands for PD-1 have been identified, PD-L1 (B7-H1) and PD-L2 (b7-DC). The activation of T cells expressing PD-1 has been shown to be downregulated upon interaction with cells expressing PD-L1 or PD-L2. Both PD-L1 and PD-L2 are B7 protein family members that bind to PD-1, but do not bind to other CD28 family members. The PD-L1 ligand is abundant in a variety of human cancers. The interaction between PD-1 and PD-L1 results in a decrease in tumor infiltrating lymphocytes, a decrease in T-cell receptor mediated proliferation, and immune evasion by the cancerous cells. Immune suppression can be reversed by inhibiting the local interaction of PD-1 with PD-L1, and the effect is additive when the interaction of PD-1 with PD-L2 is blocked as well.

PD-L1 has also been shown to interact with CD80. The interaction of PD-L1/CD80 on expressing immune cells has been shown to be an inhibitory one. Blockade of this interaction has been shown to abrogate this inhibitory interaction.

When PD-1 expressing T cells contact cells expressing its ligands, functional activities in response to antigenic stimuli, including proliferation, cytokine secretion, and cytotoxicity, are reduced. PD-1/PD-L1 or PD-L2 interactions down regulate immune responses during resolution of an infection or tumor, or during the development of self. Chronic antigen stimulation, such as that which occurs during tumor disease or chronic infections, results in T cells that express elevated levels of PD-1 and are dysfunctional with respect to activity towards the chronic antigen. This is termed "T cell exhaustion". B cells also display PD-1/PD-ligand suppression and "exhaustion".

Blockade of PD-1/PD-L1 ligation using antibodies to PD-L1 has been shown to restore and augment T cell activation in many systems. Patients with advanced cancer benefit from therapy with a monoclonal antibody to PD-L1. Preclinical animal models of tumors and chronic infections have shown that blockade of the PD-1/PD-L1 pathway by monoclonal antibodies can enhance an immune response and result in tumor rejection or control of infection. Antitumor immunotherapy via PD-1/PD-L1 blockade can augment therapeutic immune response to a number of histologically distinct tumors.

Interference with the PD-1/PD-L1 interaction causes enhanced T cell activity in systems with chronic infection. Blockade of PD-L1 caused improved viral clearance and restored immunity in mice with chromoic lymphocytic chorio meningitis virus infection. Humanized mice infected with HIV-1 show enhanced protection against viremia and viral depletion of CD4+ T cells. Blockade of PD-1/PD-L1 through monoclonal antibodies to PD-L1 can restore in vitro antigen-specific functionality to T cells from HIV patients.

Blockade of the PD-L1/CD80 interaction has also been shown to stimulate immunity. Immune stimulation resulting from blockade of the PD-L1/CD80 interaction has been shown to be enhanced through combination with blockade of further PD-1/PD-L1 or PD-1/PD-L2 interactions.

Alterations in immune cell phenotypes are hypothesized to be an important factor in septic shock. These include increased levels of PD-1 and PD-L1. Cells from septic shock patients with increased levels of PD-1 and PD-L1 exhibit an increased level of T cell apoptosis. Antibodies directed to PD-L1, can reduce the level of immune cell apoptosis. Furthermore, mice lacking PD-1 expression are more resistant to septic shock symptoms than wildtype mice. Studies have revealed that blockade of the interactions of PD-L1 using antibodies can suppress inappropriate immune responses and ameliorate disease signs.

In addition to enhancing immunologic responses to chronic antigens, blockade of the PD-1/PD-L1 pathway has also been shown to enhance responses to vaccination, including therapeutic vaccination in the context of chronic infection.

The PD-1 pathway is a key inhibitory molecule in T cell exhaustion that arises from chronic antigen stimulation during chronic infections and tumor disease. Blockade of the PD-1/PD-L1 interaction through targeting the PD-L1 protein has been shown to restore antigen-specific T cell immune functions in vitro and in vivo, including enhanced responses to vaccination in the setting of tumor or chronic infection. Accordingly, agents that block the interaction of PD-L1 with either PD-1 or CD80 are desired.

SUMMARY

The present disclosure provides macrocyclic compounds which inhibit the PD-1/PD-L1 and CD80/PD-L1 protein/protein interaction, and are thus useful for the amelioration of various diseases, including cancer and infectious diseases.

In a first aspect the present disclosure provides a compound of formula (I)

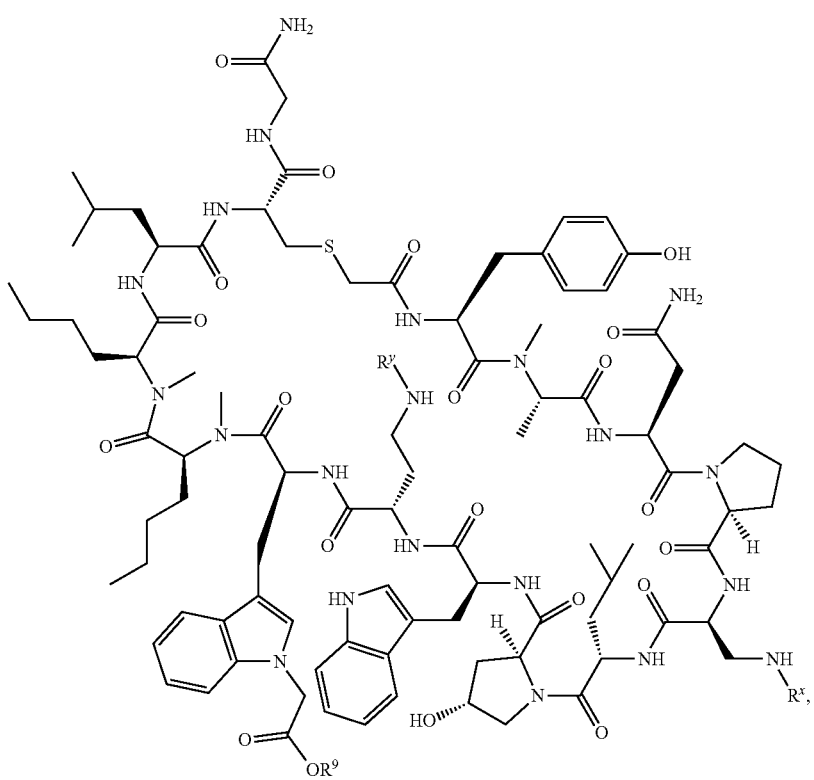

(I)

or a pharmaceutically acceptable salt thereof, wherein:
$R^x$ and $R^y$ are independently H,

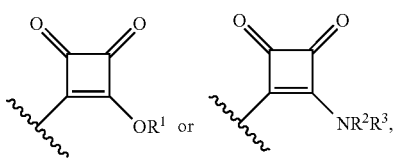

provided that at least one of $R^x$ and $R^y$ is other than H;
$R^1$ is H, halogen or $C_1$-$C_6$ alkyl;
$R^2$ and $R^3$ are independently H, halogen, $C_1$-$C_6$ alkyl, or aryl; said aryl group substituted with 0-3 $R^{3a}$;
$R^{3a}$ is halogen or $COOR^4$;
$R^4$ is H or $C_1$-$C_6$ alkyl; and
$R^9$ is H or $C_1$-$C_3$ alkyl.

In a first embodiment of the first aspect, the present disclosure provides a compound of formula (I), or a pharmaceutically acceptable salt thereof, wherein $R^x$ is H.

In a second embodiment of the first aspect, the present disclosure provides a compound of formula (I), or a pharmaceutically acceptable salt thereof, wherein $R^y$ is H.

In a third embodiment of the first aspect, the present disclosure provides a compound of formula (I), or a pharmaceutically acceptable salt thereof, wherein $R^9$ is H or —$CH_3$.

In a fourth embodiment of the first aspect, the present disclosure provides a compound of formula (I), or a pharmaceutically acceptable salt thereof, wherein
$R^2$ and $R^3$ are independently H, halogen, $C_1$-$C_6$ alkyl or phenyl; said phenyl group substituted with 0-3 $R^{3a}$;
$R^{3a}$ is halogen or $COOR^4$;
$R^4$ is H or $C_1$-$C_6$ alkyl; and
$R^9$ is H or $C_1$-$C_3$ alkyl.

In another embodiment, the present disclosure provides a compound selected from the exemplified examples within the scope of the first aspect, or a pharmaceutically acceptable salt, tautomer or stereoisomer thereof.

In another embodiment, there is provided a compound selected from any subset list of compounds within the scope of the first aspect.

In a second aspect, the present disclosure provides a method of enhancing, stimulating, and/or increasing an immune response in a subject in need thereof, wherein the method comprises administering to the subject a therapeutically effective amount of a compound of formula (I) or formula (II), or a pharmaceutically acceptable salt thereof.

In a third aspect, the present disclosure provides a method of blocking the interaction of PD-L1 with PD-1 and/or CD80 in a subject, wherein the method comprises administering to the subject a therapeutically effective amount of a compound of formula (I) or formula (II) or a pharmaceutically acceptable salt thereof.

In a fourth aspect the present disclosure provides a method of enhancing, stimulating, and/or increasing an immune response in a subject in need thereof, said method comprising administering to the subject a therapeutically effective amount of a compound of formula (I) or formula (II), or a pharmaceutically acceptable salt thereof. In a first embodiment of the second aspect the method further comprises administering an additional agent prior to, after, or simultaneously with the compound of formula (I), compound of formula (I), or a pharmaceutically acceptable salt thereof. In a second embodiment the additional agent is selected from an antimicrobial agent, an antiviral agent, a cytotoxic agent, a TLR7 agonist, a TLR8 agonist, an HDAC inhibitor, and an immune response modifier.

In a fifth aspect the present disclosure provides a method of inhibiting growth, proliferation, or metastasis of cancer cells in a subject in need thereof, said method comprising administering to the subject a therapeutically effective amount a compound of formula (I) or formula (II), or a pharmaceutically acceptable salt thereof. In a first embodiment of the third aspect the cancer is selected from melanoma, renal cell carcinoma, squamous non-small cell lung cancer (NSCLC), non-squamous NSCLC, colorectal cancer, castration-resistant prostate cancer, ovarian cancer, gastric cancer, hepatocellular carcinoma, pancreatic carcinoma, squamous cell carcinoma of the head and neck, carcinomas of the esophagus, gastrointestinal tract and breast, and hematological malignancies.

In a sixth aspect the present disclosure provides a method of treating an infectious disease in a subject in need thereof, the method comprising administering to the subject a therapeutically effective amount of a compound of formula (I) or formula (II), or a pharmaceutically acceptable salt thereof. In a first embodiment of the fourth aspect the infectious disease is caused by a virus. In a second embodiment the virus is selected from HIV, Hepatitis A, Hepatitis B, Hepatitis C, herpes viruses, and influenza.

In a seventh aspect the present disclosure provides a method of treating septic shock in a subject in need thereof, the method comprising administering to the subject a therapeutically effective amount of a compound of formula (I) or formula (II), or a pharmaceutically acceptable salt thereof.

In an eighth aspect the present disclosure provides a method of blocking the interaction of PD-L1 with PD-1 and/or CD80 in a subject, said method comprising administering to the subject a therapeutically effective amount of a compound of formula (I) or formula (II), or a pharmaceutically acceptable salt thereof.

DETAILED DESCRIPTION

Unless otherwise indicated, any atom with unsatisfied valences is assumed to have hydrogen atoms sufficient to satisfy the valences.

The singular forms "a," "an," and "the" include plural referents unless the context dictates otherwise.

As used herein, the term "or" is a logical disjunction (i.e., and/or) and does not indicate an exclusive disjunction unless expressly indicated such as with the terms "either," "unless," "alternatively," and words of similar effect.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-4}$ alkyl" denotes straight and branched chain alkyl groups with one to four carbon atoms.

The term "aryl" as used herein, refers to a group of atoms derived from a molecule containing aromatic ring(s) by removing one hydrogen that is bonded to the aromatic ring(s). Representative examples of aryl groups include, but are not limited to, phenyl and naphthyl. The aryl ring may be unsubstituted or may contain one or more substituents as valence allows.

The term "haloalkyl" which includes the term "fluoroalkyl" as used herein is intended to include both branched and straight-chain saturated aliphatic hydrocarbon groups substituted with one or more fluorine atoms. For example, "$C_{1-4}$ fluoroalkyl" is intended to include $C_1$, $C_2$, $C_3$, and $C_4$ alkyl groups substituted with one or more fluorine atoms. Representative examples of fluoroalkyl groups include, but are not limited to, —$CF_3$ and —$CH_2CF_3$.

The terms "halo" and "halogen", as used herein, refer to F, Cl, Br, or I.

As used herein, the phrase "or a pharmaceutically acceptable salt thereof" refers to at least one compound, or at least one salt of the compound, or a combination thereof. For example, "a compound of Formula (I) or a pharmaceutically acceptable salt thereof" includes, but is not limited to, a compound of Formula (I), two compounds of Formula (I), a pharmaceutically acceptable salt of a compound of Formula (I), a compound of Formula (I) and one or more pharmaceutically acceptable salts of the compound of Formula (I), and two or more pharmaceutically acceptable salts of a compound of Formula (I).

An "adverse event" or "AE" as used herein is any unfavorable and generally unintended, even undesirable, sign (including an abnormal laboratory finding), symptom, or disease associated with the use of a medical treatment. For example, an adverse event can be associated with activation of the immune system or expansion of immune system cells (e.g., T cells) in response to a treatment. A medical treatment can have one or more associated AEs and each AE can have the same or different level of severity. Reference to methods capable of "altering adverse events" means a treatment regime that decreases the incidence and/or severity of one or more AEs associated with the use of a different treatment regime.

As used herein, "hyperproliferative disease" refers to conditions wherein cell growth is increased over normal levels. For example, hyperproliferative diseases or disorders include malignant diseases (e.g., esophageal cancer, colon cancer, biliary cancer) and non-malignant diseases (e.g., atherosclerosis, benign hyperplasia, and benign prostatic hypertrophy).

The term "immune response" refers to the action of, for example, lymphocytes, antigen presenting cells, phagocytic cells, granulocytes, and soluble macromolecules that results in selective damage to, destruction of, or elimination from the human body of invading pathogens, cells or tissues infected with pathogens, cancerous cells, or, in cases of autoimmunity or pathological inflammation, normal human cells or tissues.

The terms "Programmed Death Ligand 1", "Programmed Cell Death Ligand 1", "PD-L1", "PDL1", "hPD-L1", "hPD-L1", and "B7-H1" are used interchangeably, and include variants, isoforms, species homologs of human PD-L1, and analogs having at least one common epitope with PD-L1. The complete PD-L1 sequence can be found under GENBANK® Accession No. NP_054862.

The terms "Programmed Death 1", "Programmed Cell Death 1", "Protein PD-1", "PD-1", "PD1", "hPD-1" and "hPD-I" are used interchangeably, and include variants, isoforms, species homologs of human PD-1, and analogs having at least one common epitope with PD-1. The complete PD-1 sequence can be found under GENBANK® Accession No. U64863.

The term "treating" refers to inhibiting the disease, disorder, or condition, i.e., arresting its development; and (iii) relieving the disease, disorder, or condition, i.e., causing regression of the disease, disorder, and/or condition and/or symptoms associated with the disease, disorder, and/or condition.

The present disclosure is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the disclosure can generally be prepared by conventional techniques known to those skilled in the art or by processes analogous to those described herein, using an appropriate isotopically-labeled reagent in place of the non-labeled reagent otherwise employed. Such compounds can have a variety of potential uses, for example as standards and reagents in determining biological activity. In the case of stable isotopes, such compounds can have the potential to favorably modify biological, pharmacological, or pharmacokinetic properties.

An additional aspect of the subject matter described herein is the use of the disclosed compounds as radiolabeled ligands for development of ligand binding assays or for monitoring of in vivo adsorption, metabolism, distribution, receptor binding or occupancy, or compound disposition. For example, a macrocyclic compound described herein can be prepared using a radioactive isotope and the resulting radiolabeled compound can be used to develop a binding assay or for metabolism studies. Alternatively, and for the same purpose, a macrocyclic compound described herein can be converted to a radiolabeled form by catalytic tritiation using methods known to those skilled in the art.

The macrocyclic compounds of the present disclosure can also be used as PET imaging agents by adding a radioactive tracer using methods known to those skilled in the art.

Those of ordinary skill in the art are aware that an amino acid includes a compound represented by the general structure:

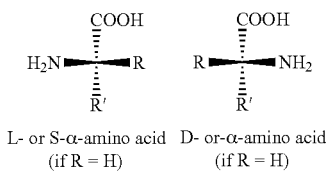

L- or S-α-amino acid (if R = H)   D- or-α-amino acid (if R = H)

where R and R' are as discussed herein. Unless otherwise indicated, the term "amino acid" as employed herein, alone or as part of another group, includes, without limitation, an amino group and a carboxyl group linked to the same carbon, referred to as "α" carbon, where R and/or R' can be a natural or an un-natural side chain, including hydrogen. The absolute "S" configuration at the "α" carbon is commonly referred to as the "L" or "natural" configuration. In the case where both the "R" and the "R'"(prime) substituents equal hydrogen, the amino acid is glycine and is not chiral.

Where not specifically designated, the amino acids described herein can be D- or L-stereochemistry and can be substituted as described elsewhere in the disclosure. It should be understood that when stereochemistry is not specified, the present disclosure encompasses all stereochemical isomeric forms, or mixtures thereof, which possess the ability to inhibit the interaction between PD-1 and PD-L1 and/or CD80 and PD-L1. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

Certain compounds of the present disclosure can exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

Certain compounds of the present disclosure can exist as tautomers, which are compounds produced by the phenomenon where a proton of a molecule shifts to a different atom within that molecule. The term "tautomer" also refers to one of two or more structural isomers that exist in equilibrium and are readily converted from one isomer to another. All tautomers of the compounds described herein are included within the present disclosure.

The pharmaceutical compounds of the disclosure can include one or more pharmaceutically acceptable salts. A "pharmaceutically acceptable salt" refers to a salt that retains the desired biological activity of the parent compound and does not impart any undesired toxicological effects (see e.g., Berge, S. M. et al., *J. Pharm. Sci.*, 66:1-19 (1977)). The salts can be obtained during the final isolation and purification of the compounds described herein, or separately be reacting a free base function of the compound with a suitable acid or by reacting an acidic group of the compound with a suitable base. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

Administration of a therapeutic agent described herein includes, without limitation, administration of a therapeutically effective amount of therapeutic agent. The term "therapeutically effective amount" as used herein refers, without limitation, to an amount of a therapeutic agent to treat a condition treatable by administration of a composition comprising the PD-1/PD-L1 binding inhibitors described herein. That amount is the amount sufficient to exhibit a detectable therapeutic or ameliorative effect. The effect can include, for example and without limitation, treatment of the conditions listed herein. The precise effective amount for a subject will depend upon the subject's size and health, the nature and extent of the condition being treated, recommendations of the treating physician, and therapeutics or combination of therapeutics selected for administration. Thus, it is not useful to specify an exact effective amount in advance.

In another aspect, the disclosure pertains to methods of inhibiting growth of tumor cells in a subject using the macrocyclic compounds of the present disclosure. As demonstrated herein, the compounds of the present disclosure are capable of binding to PD-L1, disrupting the interaction between PD-L1 and PD-1, competing with the binding of PD-L1 with anti-PD-1 monoclonal antibodies that are known to block the interaction with PD-1, enhancing CMV-specific T cell IFNγ secretion, and enhancing HIV-specific T cell IFNγ secretion. As a result, the compounds of the present disclosure are useful for modifying an immune response, treating diseases such as cancer or infectious disease, stimulating a protective autoimmune response or to stimulate antigen-specific immune responses (e.g., by co-administration of PD-L1 blocking compounds with an antigen of interest).

Pharmaceutical Compositions

In another aspect, the present disclosure provides a composition, e.g., a pharmaceutical composition, containing one or a combination of the compounds described within the present disclosure, formulated together with a pharmaceutically acceptable carrier. Pharmaceutical compositions of the disclosure also can be administered in combination therapy, i.e., combined with other agents. For example, the combination therapy can include a macrocyclic compound combined with at least one other anti-inflammatory or immunosuppressant agent. Examples of therapeutic agents that can be used in combination therapy are described in greater detail below in the section on uses of the compounds of the disclosure.

As used herein, "pharmaceutically acceptable carrier" includes any and all solvents, dispersion media, coatings, antibacterial and antifungal agents, isotonic and absorption delaying agents, and the like that are physiologically compatible. In some embodiments, the carrier is suitable for intravenous, intramuscular, subcutaneous, parenteral, spinal or epidermal administration (e.g., by injection or infusion). Depending on the route of administration, the active compound can be coated in a material to protect the compound from the action of acids and other natural conditions that can inactivate the compound.

A pharmaceutical composition of the disclosure also can include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

The pharmaceutical compositions of the present disclosure can be administered via one or more routes of administration using one or more of a variety of methods known in the art. As will be appreciated by the skilled artisan, the route and/or mode of administration will vary depending upon the desired results. In some embodiments, the routes of administration for macrocyclic compounds of the disclosure include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, some methods of preparation are vacuum drying and freeze-drying (lyophilization) that yield a powder of the active ingredient plus any additional desired ingredient from a previously sterile-filtered solution thereof.

Examples of suitable aqueous and non-aqueous carriers that can be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions can also contain adjuvants such as preservatives, wetting agents, emulsifying agents and dispersing agents. Prevention of presence of microorganisms can be ensured both by sterilization procedures, supra, and by the inclusion of various antibacterial and antifungal agents, for example, paraben, chlorobutanol, phenol sorbic acid, and the like. It can also be desirable to include isotonic agents, such as sugars, sodium chloride, and the like into the compositions. In addition, prolonged absorption of the injectable pharmaceutical form can be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the disclosure is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be desirable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Alternatively, the compounds of the disclosure can be administered via a non-parenteral route, such as a topical, epidermal or mucosal route of administration, for example, intranasally, orally, vaginally, rectally, sublingually or topically.

Any pharmaceutical composition contemplated herein can, for example, be delivered orally via any acceptable and suitable oral preparation. Exemplary oral preparations include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the disclosure can contain at least one agent selected from sweetening agents, flavoring agents, coloring agents, demulcents, anti-oxidants, and preserving agents.

A tablet can, for example, be prepared by admixing at least one compound of Formula (I) and/or at least one pharmaceutically acceptable salt thereof with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials include, but are not limited to, hydroxypropyl-methyl-cellulose and hydroxypropyl-cellulose. Exemplary time delay materials include, but are not limited to, ethyl cellulose and cellulose acetate butyrate.

Hard gelatin capsules can, for example, be prepared by mixing at least one compound of Formula (I) and/or at least one salt thereof with at least one inert solid diluent, such as, for example, calcium carbonate; calcium phosphate; and kaolin.

Soft gelatin capsules can, for example, be prepared by mixing at least one compound of Formula (I) and/or at least one pharmaceutically acceptable salt thereof with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) and/or at least one pharmaceutically acceptable salt thereof with at least one excipient suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example, heptadecathylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) and/or at least one pharmaceutically acceptable salt thereof in either a vegetable oil, such as, for example, arachis oil, sesame oil, and coconut oil; or in mineral oil, such as, for example, liquid paraffin. An oily suspension can also contain at least one thickening agent, such as, for example, beeswax, hard paraffin, and cetyl alcohol. In order to provide a palatable oily suspension, at least one of the sweetening agents already described herein above, and/or at least one flavoring agent can be added to the oily suspension. An oily suspension can further contain at least one preservative, including, but not limited to, for example, an anti-oxidant, such as, for example, butylated hydroxyanisol, and alpha-tocopherol.

Dispersible powders and granules can, for example, be prepared by admixing at least one compound of Formula (I) and/or at least one pharmaceutically acceptable salt thereof with at least one dispersing and/or wetting agent, at least one suspending agent, and/or at least one preservative. Suitable dispersing agents, wetting agents, and suspending agents are already described above. Exemplary preservatives include, but are not limited to, for example, anti-oxidants, e.g., ascorbic acid. In addition, dispersible powders and granules can also contain at least one excipient, including, but not limited to, for example, sweetening agents, flavoring agents, and coloring agents.

An emulsion of at least one compound of Formula (I) and/or at least one pharmaceutically acceptable salt thereof can, for example, be prepared as an oil-in-water emulsion. The oily phase of the emulsions comprising the compounds of Formula (I) can be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase can comprise merely an emulsifier, it can comprise a mixture of at least none emulsifier with a fat or an oil or with both a fat and an oil. Suitable emulsifying agents include, but are not limited to, for example, naturally-occurring phosphatides, e.g., soy bean lecithin, esters or partial esters derived from fatty acids and hexitol anhydrides, such as, for example sorbitan monoleate, and condensation products of partial esters with ethylene oxide, such as, for example, polyoxy-ethylene sorbitan monooleate. In some embodiments, a hydrophilic emulsifier is included together with a lipophilic emulsifier which acts as a stabilizer. It is also sometimes desirable to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present disclosure include Tween 60, Span 80, cetostearyl alcohol, myristyl alcohol, glyceryl monostearate, sodium lauryl sulfate, glyceral disterate alone or with a wax, or other materials well known in the art.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Robinson, J. R., ed., *Sustained and Controlled Release Drug Delivery Systems*, Marcel Dekker, Inc., New York (1978).

Therapeutic compositions can be administered with medical devices known in the art. For example, in one embodiment, a therapeutic composition of the disclosure can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the present disclosure include: U.S. Pat. No. 4,487,603, which discloses an implantable micro-infusion pump for dispensing medication at a controlled rate; U.S. Pat. No. 4,486,194, which discloses a therapeutic device for administering medication through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the compounds of the disclosure can be formulated to ensure proper distribution in vivo. For example, the blood-brain barrier (BBB) excludes many highly hydrophilic compounds. To ensure that therapeutic compounds of the disclosure cross the BBB (if desired), they can be formulated, for example, in liposomes. For methods of manufacturing liposomes, see, e.g., U.S. Pat. Nos. 4,522, 811, 5,374,548, and 5,399,331. The liposomes can comprise one or more moieties which are selectively transported into specific cells or organs, thus enhance targeted drug delivery (see, e.g., Ranade, V. V., *J. Clin. Pharmacol.*, 29:685 (1989)). Exemplary targeting moieties include folate or biotin (see, e.g., U.S. Pat. No. 5,416,016 to Low et al.); mannosides (Umezawa et al., *Biochem. Biophys. Res. Commun.*, 153:1038 (1988)); macrocyclic compounds (Bloeman, P. G. et al., *FEBS Lett.*, 357:140 (1995); Owais, M. et al., *Antimicrob. Agents Chemother.*, 39:180 (1995)); surfactant protein A receptor (Briscoe et al., *Am. J. Physiol.*, 1233:134 (1995)); p 120 (Schreier et al., *J. Biol. Chem.*, 269:9090 (1994)); see also Keinanen, K. et al., *FEBS Lett.*, 346:123 (1994); Killion, J. J. et al., *Immunomethods* 4:273 (1994).

SYNTHETIC METHODS

The compounds may be made by methods known in the art including those described below and including variations within the skill of the art. Some reagents and intermediates are known in the art. Other reagents and intermediates can be made by methods known in the art using readily available materials. The variables (e.g. numbered "R" substituents) used to describe the synthesis of the compounds are intended only to illustrate how to make the compounds and are not to be confused with variables used in the claims or in other sections of the specification. The following methods are for illustrative purposes and are not intended to limit the scope of the invention.

Abbreviations used in the schemes generally follow conventions used in the art. Chemical abbreviations used in the specification and examples are defined as follows: "THF" for tetrahydrofuran; "DMF" for N,N-dimethylformamide; "MeOH" for methanol; "EtOH" for ethanol; "n-PrOH" for 1-propyl alcohol or propan-1-ol; "i-PrOH" for 2-propyl alcohol or propan-2-ol; "Ar" for aryl; "TFA" for trifluoroacetic acid; "DMSO" for dimethylsulfoxide; "EtOAc" for ethyl acetate; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "h" for hours; "rt" for room temperature or retention time (context will dictate); "min" for minutes; "HOBt" for 1-hydroxybenzotriazole hydrate; "HCTU" for 1-[bis(dimethylamino)methylen]-5-chlorobenzotriazolium 3-oxide hexafluorophosphate or N,N,N',N'-tetramethyl-O-(6-chloro-1H-benzotriazol-1-yl)uronium hexafluorophosphate; "HATU" for 1-[bis(dimethylamino)methylene]-1H-1,2,3-triazolo [4,5-b]pyridinium 3-oxid hexafluorophosphate or N-[(dimethylamino)-1H-1,2,3-triazolo-[4,5-b]pyridin-1-yl-methylene]-N-methylmethanaminium hexafluorophosphate N-oxide; "DIEA" and "iPrNEt$_2$" for diisopropylethylamine; "Et$_3$N" for triethyl amine.

Abbreviations are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LC" for liquid chromatography, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

BMT-001's structure is
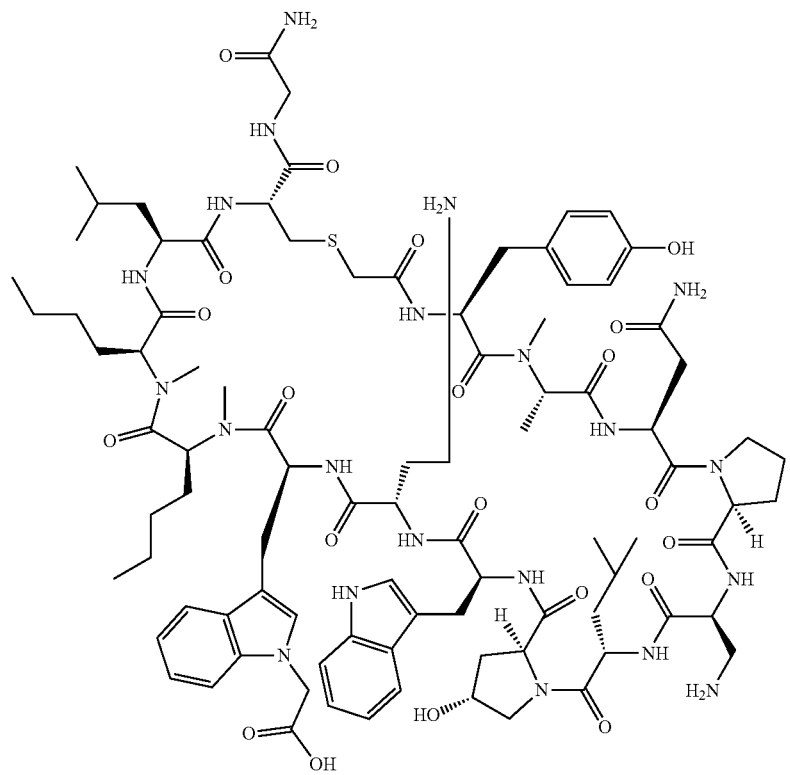 [SMILES: CCCC[C@H]1C(=O)N(C)[C@@H](CCCC)C(=O)N[C@@H](CC(C)C)C(=O)N[C@H](C(=O)NCC(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]
BMT-002's structure is
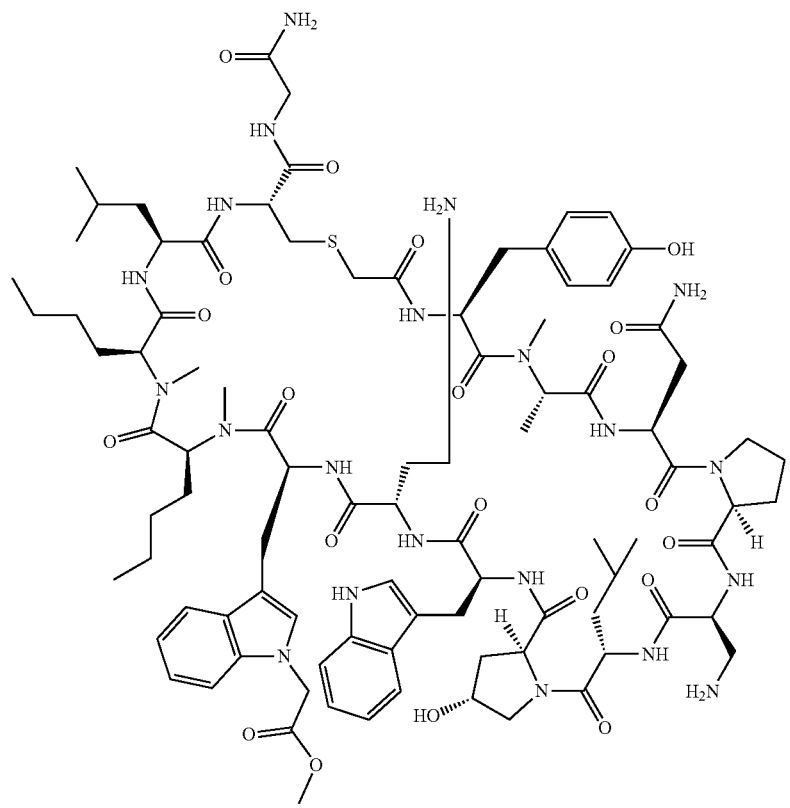 [SMILES: CCCC[C@H]1C(=O)N(C)[C@@H](CCCC)C(=O)N[C@@H](CC(C)C)C(=O)N[C@H](C(=O)NCC(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)OC)c3ccccc23)C(=O)N1C]

General Procedure for the Preparation of the Structures of Claim I

A solution of BMT-001 or BMT-002 and electrophile in MeOH or EtOH or n-PrOH or i-PrOH was stirred at room temperature to 100° C. for 0.5-48 hours. After all the solvents were removed under vacuum, the residue was purified by the preparative HPLC to give the compounds of Claim I.

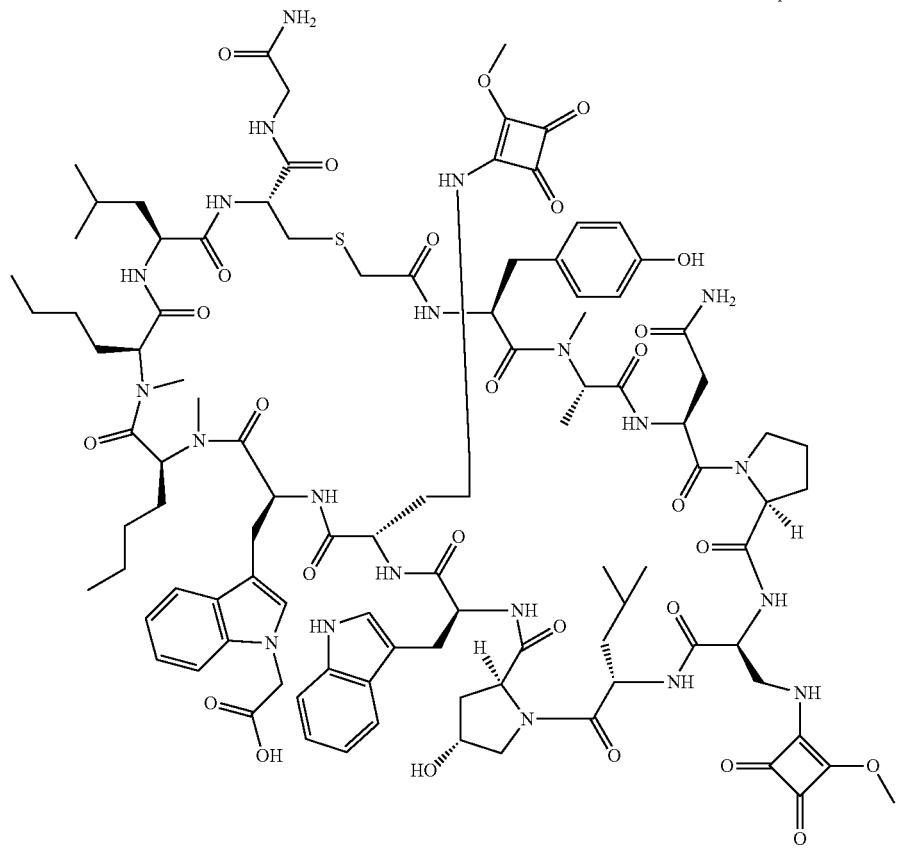

Compound 1001

| Agents Used | |
|---|---|
| Starting Material | BMT-001 |
| Electrophile | 3,4-Dimethoxycyclobut-3-ene-1,2-dione |
| MS | |
| MS (M/2 + H)+ Calcd. | 1054 |
| MS (M/2 + H)+ Observ. | 1054 |
| Retention Time | 1.55 min |
| LC Condition | |
| Solvent A | 5:95 acetonitrile:water with 10 mM ammonium acetate |
| Solvent B | 95:5 acetonitrile:water with 10 mM ammonium acetate |
| Start % B | 0 |
| Final % B | 100 |
| Gradient Time | 3 min |
| Flow Rate | 1 mL/min |
| Wavelength | 220 |
| Temperature | 50° C. |
| Column | Waters Acquity UPLC BEH C18, 2.1 × 50 mm, 1.7-μm particles |

Compound 1002

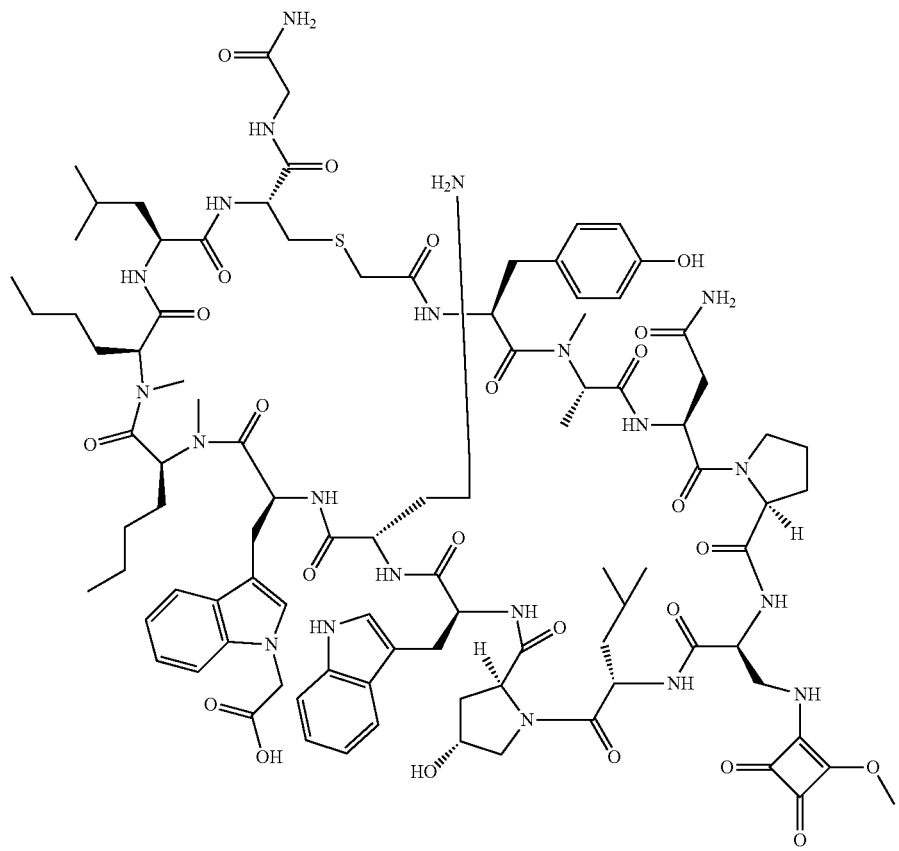 [SMILES: CCCC[C@H]1C(=O)N(C)[C@@H](CCCC)C(=O)N[C@@H](CC(C)C)C(=O)N[C@H](C(=O)NCC(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CNc2c(OC)c(=O)c2=O)C(=O)N[C@@H](CC(C)C)C(=O)N2C[C@H](O)C[C@H]2C(=O)N[C@@H](Cc2c[nH]c3ccccc23)C(=O)N[C@@H](CCCN)C(=O)N[C@@H](Cc2cn(CC(=O)O)c3ccccc23)C(=O)N1C]

| Agents Used | |
|---|---|
| Starting Material | BMT-001 |
| Electrophile | 3,4-Dimethoxycyclobut-3-ene-1,2-dione |
| MS | |
| MS (M/2 + H)+ Calcd. | 999 |
| MS (M/2 + H)+ Observ. | 999 |
| Retention Time | 1.66 min |
| LC Condition | |
| Solvent A | 5:95 acetonitrile:water with 10 mM ammonium acetate |
| Solvent B | 95:5 acetonitrile:water with 10 mM ammonium acetate |
| Start % B | 0 |
| Final % B | 100 |
| Gradient Time | 3 min |
| Flow Rate | 1 mL/min |
| Wavelength | 220 |
| Temperature | 50° C. |
| Column | Waters Acquity UPLC BEH C18, 2.1 × 50 mm, 1.7-μm particles |

Compound 1003

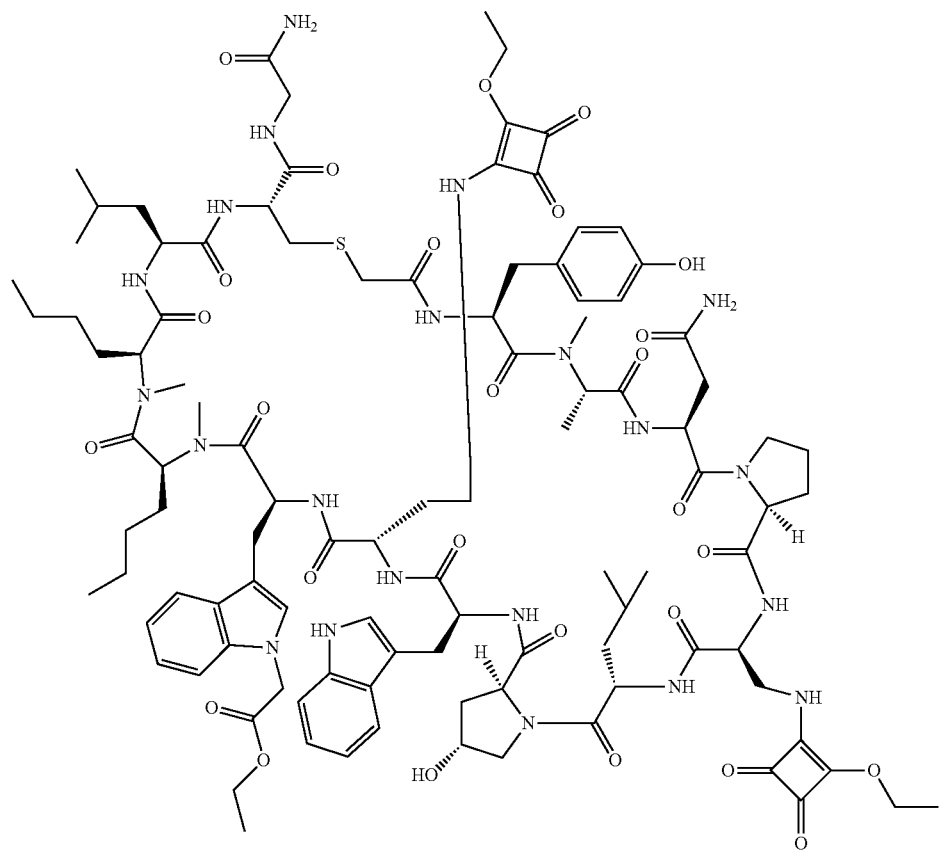 [SMILES: CCCC[C@H]1C(=O)N(C)[C@@H](CCCC)C(=O)N[C@@H](CC(C)C)C(=O)N[C@H](C(=O)NCC(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CNc2c(OCC)c(=O)c2=O)C(=O)N[C@@H](CC(C)C)C(=O)N2C[C@H](O)C[C@H]2C(=O)N[C@@H](Cc2c[nH]c3ccccc23)C(=O)N[C@@H](CCCNc2c(OCC)c(=O)c2=O)C(=O)N[C@@H](Cc2cn(CC(=O)OCC)c3ccccc23)C(=O)N1C]

| Agents Used | |
|---|---|
| Starting Material | BMT-001 |
| Electrophile | 3,4-Dimethoxycyclobut-3-ene-1,2-dione |
| MS | |
| MS (M/2 + H)+ Calcd. | 1082 |
| MS (M/2 + H)+ Observ. | 1082 |
| Retention Time | 1.92 min |
| LC Condition | |
| Solvent A | 5:95 acetonitrile:water with 10 mM ammonium acetate |
| Solvent B | 95:5 acetonitrile:water with 10 mM ammonium acetate |
| Start % B | 0 |
| Final % B | 100 |
| Gradient Time | 3 min |
| Flow Rate | 0.75 mL/min |
| Wavelength | 220 |
| Temperature | 70° C. |
| Column | Waters XBridge C18, 2.1 mm × 50 mm, 1.7 μm particles |

Compound 1004

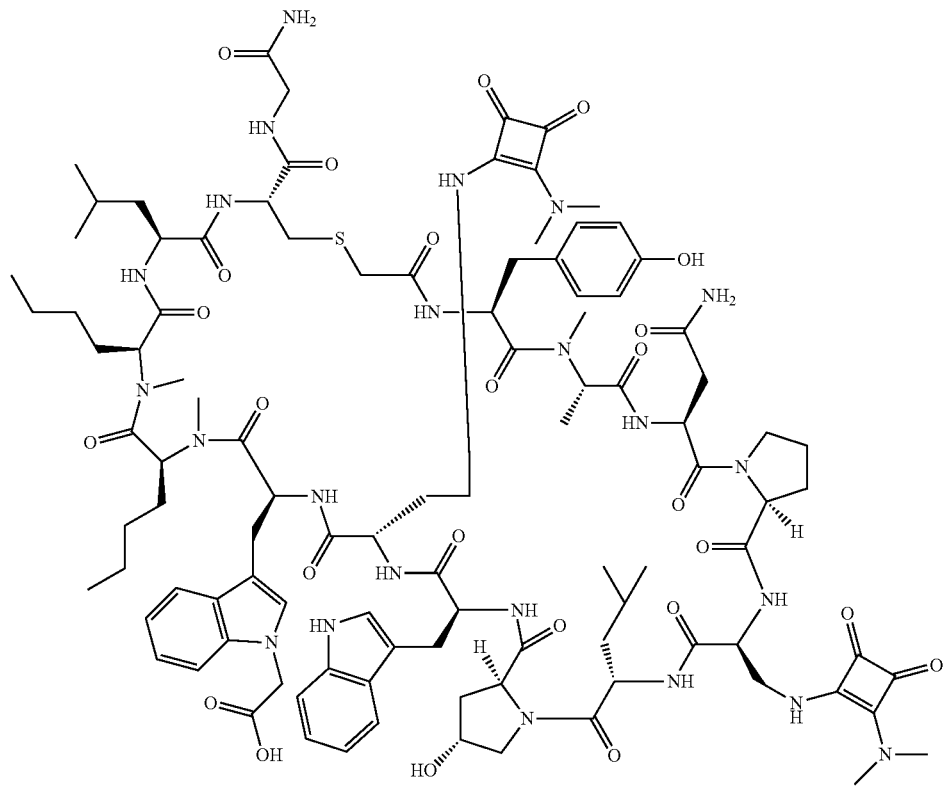 [SMILES: CCCC[C@H]1C(=O)N(C)[C@@H](CCCC)C(=O)N[C@@H](CC(C)C)C(=O)N[C@H](C(=O)NCC(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CNc2c(N(C)C)c(=O)c2=O)C(=O)N[C@@H](CC(C)C)C(=O)N2C[C@H](O)C[C@H]2C(=O)N[C@@H](Cc2c[nH]c3ccccc23)C(=O)N[C@@H](CCCNc2c(N(C)C)c(=O)c2=O)C(=O)N[C@@H](Cc2cn(CC(=O)O)c3ccccc23)C(=O)N1C]

| Agents Used | |
|---|---|
| Starting Material | BMT-001 |
| Electrophile | 3-(Dimethylamino)-4-methoxycyclobut-3-ene-1,2-dione |
| MS | |
| MS (M/2 + H)+ Calcd. | 1067 |
| MS (M/2 + H)+ Observ. | 1067 |
| Retention Time | 1.48 min |
| LC Condition | |
| Solvent A | 5:95 acetonitrile:water with 10 mM ammonium acetate |
| Solvent B | 95:5 acetonitrile:water with 10 mM ammonium acetate |
| Start % B | 0 |
| Final % B | 100 |
| Gradient Time | 3 min |
| Flow Rate | 1 mL/min |
| Wavelength | 220 |
| Temperature | 50° C. |
| Column | Waters XBridge C18, 2.1 mm × 50 mm, 1.7 μm particles |

Compound 1005

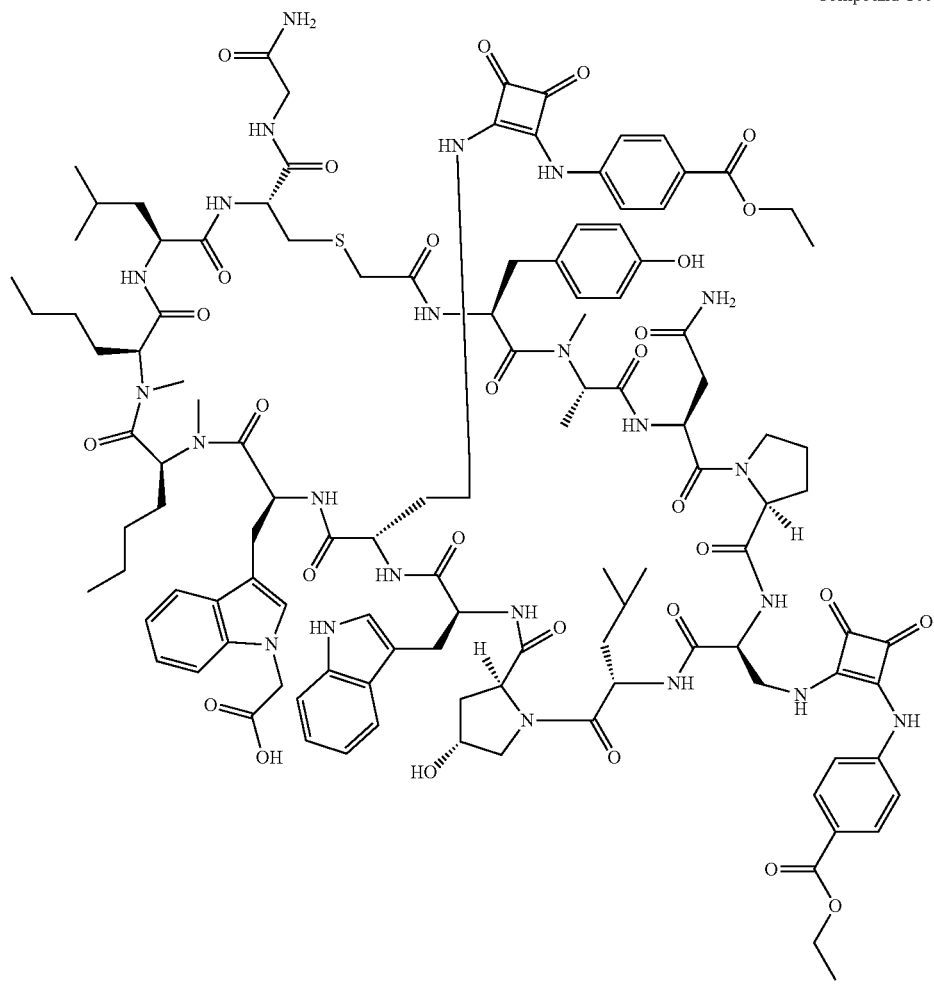

| Agents Used | |
|---|---|
| Starting Material | BMT-001 |
| Electrophile | Ethyl 4-((2-ethoxy-3,4-dioxocyclobut-1-en-1-yl)amino)benzoate |
| MS | |
| MS (M/2 + H)+ Calcd. | 1187 |
| MS (M/2 + H)+ Observ. | 1187 |
| Retention Time | 1.91 min |
| LC Condition | |
| Solvent A | 5:95 acetonitrile:water with 10 mM ammonium acetate |
| Solvent B | 95:5 acetonitrile:water with 10 mM ammonium acetate |
| Start % B | 0 |
| Final % B | 100 |
| Gradient Time | 3 min |
| Flow Rate | 1 mL/min |
| Wavelength | 220 |
| Temperature | 50 °C |
| Column | Waters XBridge C18, 2.1 mm × 50 mm, 1.7 µm particles |

Compound 1006

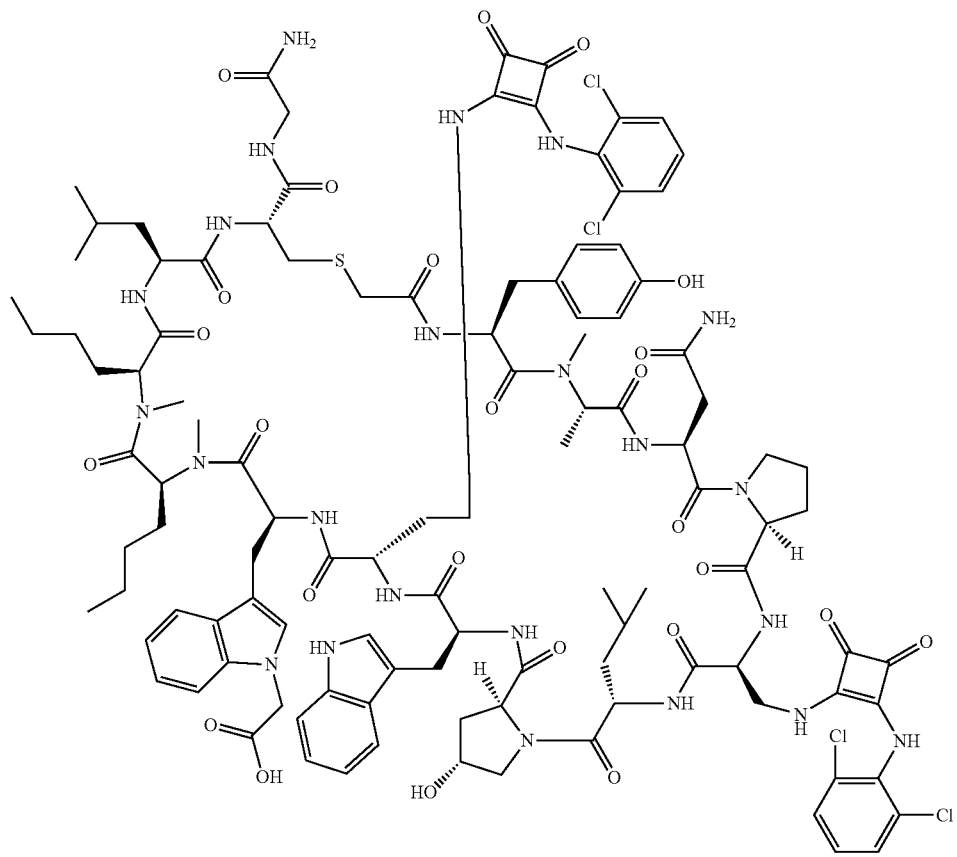 [SMILES: CCCC[C@H]1C(=O)N(C)[C@@H](CCCC)C(=O)N[C@@H](CC(C)C)C(=O)N[C@H](C(=O)NCC(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CNc2c(Nc3c(Cl)cccc3Cl)c(=O)c2=O)C(=O)N[C@@H](CC(C)C)C(=O)N2C[C@H](O)C[C@H]2C(=O)N[C@@H](Cc2c[nH]c3ccccc23)C(=O)N[C@@H](CCCNc2c(Nc3c(Cl)cccc3Cl)c(=O)c2=O)C(=O)N[C@@H](Cc2cn(CC(=O)O)c3ccccc23)C(=O)N1C]

| Agents Used | |
|---|---|
| Starting Material | BMT-001 |
| Electrophile | 3-((2,6-Dichlorophenyl)amino)-4-methoxycyclobut-3-ene-1,2-dione |
| MS | |
| MS (M/2 + H)+ Calcd. | 1183 |
| MS (M/2 + H)+ Observ. | 1183 |
| Retention Time | 1.82 min |
| LC Condition | |
| Solvent A | 5:95 acetonitrile:water with 10 mM ammonium acetate |
| Solvent B | 95:5 acetonitrile:water with 10 mM ammonium acetate |
| Start % B | 0 |
| Final % B | 100 |
| Gradient Time | 3 min |
| Flow Rate | 0.75 mL/min |
| Wavelength | 220 |
| Temperature | 70° C. |
| Column | Waters BEH C18, 2.1 × 50 mm, 1.7-μm particlesparticles |

Compound 1007
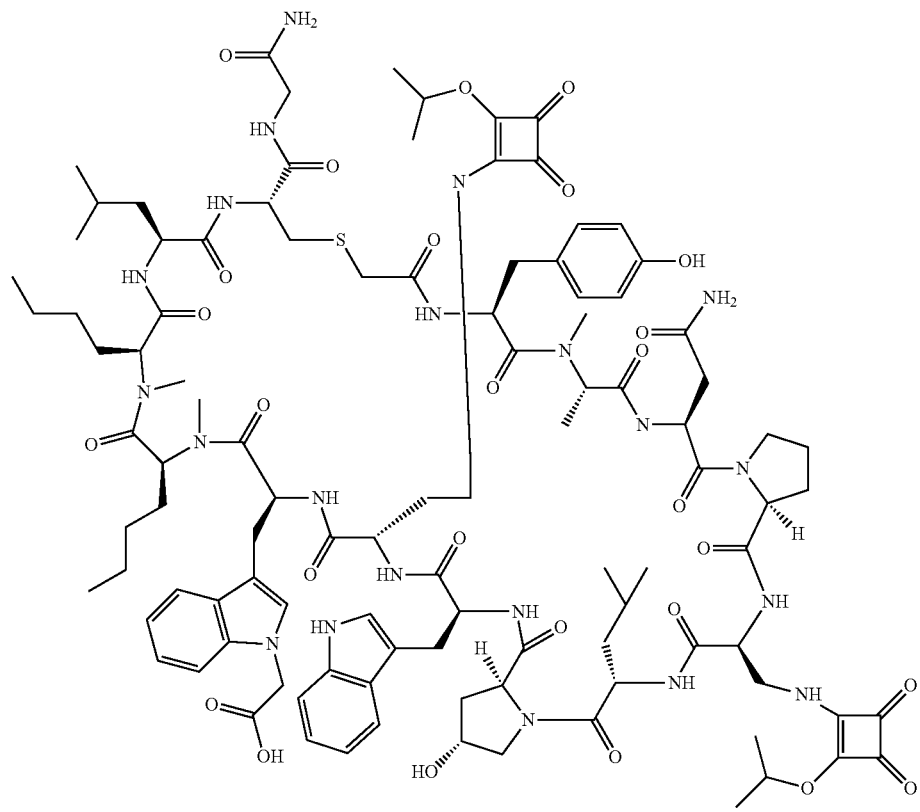 [SMILES: CCCC[C@H]1C(=O)N(C)[C@@H](CCCC)C(=O)N[C@@H](CC(C)C)C(=O)N[C@H](C(=O)NCC(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CNc2c(OC(C)C)c(=O)c2=O)C(=O)N[C@@H](CC(C)C)C(=O)N2C[C@H](O)C[C@H]2C(=O)N[C@@H](Cc2c[nH]c3ccccc23)C(=O)N[C@@H](CCCNc2c(OC(C)C)c(=O)c2=O)C(=O)N[C@@H](Cc2cn(CC(=O)O)c3ccccc23)C(=O)N1C]
| Agents Used | |
|---|---|
| Starting Material | BMT-001 |
| Electrophile | 3,4-Diisopropoxycyclobut-3-ene-1,2-dione |
| MS | |
| MS (M/2 + H)+ Calcd. | 1082 |
| MS (M/2 + H)+ Observ. | 1082 |
| Retention Time | 1.48 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Temperature | 40° C. |
| Column | Phenomenex LUNA C18, 30 × 2, 3u |

Compound 1008

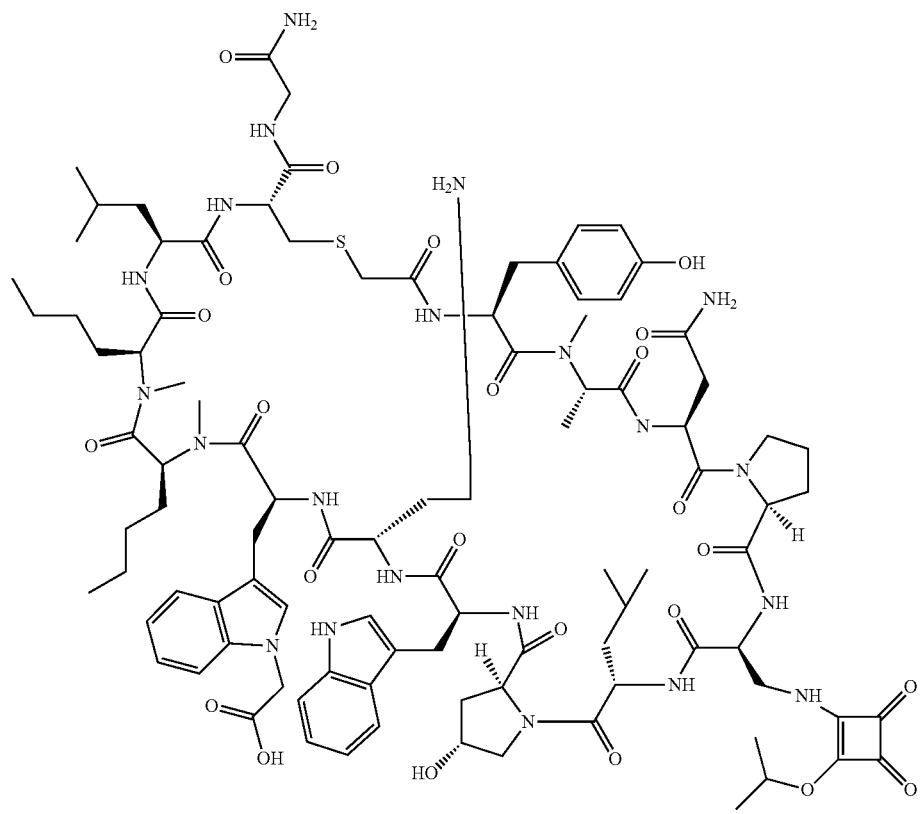 [SMILES: CCCC[C@H]1C(=O)N(C)[C@@H](CCCC)C(=O)N[C@@H](CC(C)C)C(=O)N[C@H](C(=O)NCC(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CNc2c(OC(C)C)c(=O)c2=O)C(=O)N[C@@H](CC(C)C)C(=O)N2C[C@H](O)C[C@H]2C(=O)N[C@@H](Cc2c[nH]c3ccccc23)C(=O)N[C@@H](CCCN)C(=O)N[C@@H](Cc2cn(CC(=O)O)c3ccccc23)C(=O)N1C]

| Agents Used | |
|---|---|
| Starting Material | BMT-001 |
| Electrophile | 3,4-Diisopropoxycyclobut-3-ene-1,2-dione |
| MS | |
| MS (M/2 + H)+ Calcd. | 1013 |
| MS (M/2 + H)+ Observ. | 1013 |
| Retention Time | 1.66 min |
| LC Condition | |
| Solvent A | 5:95 acetonitrile:water with 10 mM ammonium acetate |
| Solvent B | 95:5 acetonitrile:water with 10 mM ammonium acetate |
| Start % B | 0 |
| Final % B | 100 |
| Gradient Time | 3 min |
| Flow Rate | 1 mL/min |
| Wavelength | 220 |
| Temperature | 50° C. |
| Column | Waters XBridge C18, 2.1 mm × 50 mm, 1.7 μm particles |

Compound 1009

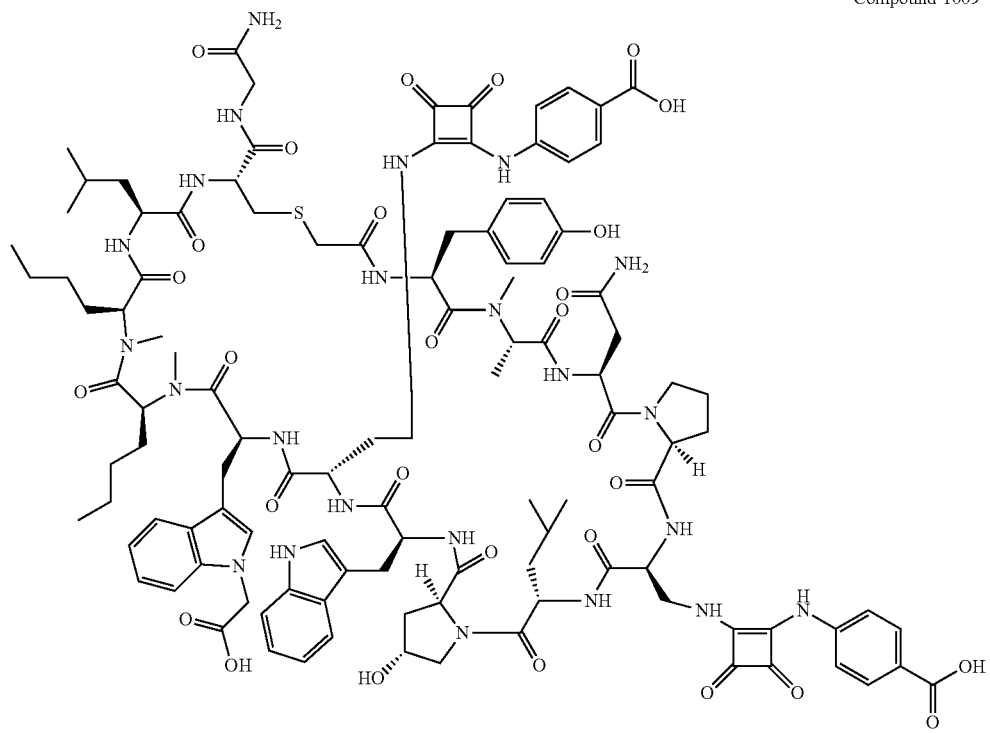

| Agents Used | |
| --- | --- |
| Starting Material | BMT-001 |
| Electrophile | 4-((2-Ethoxy-3,4-dioxocyclobut-1-en-1-yl)amino)benzoic acid |
| MS | |
| MS (M/2 + H)+ Calcd. | 1159 |
| MS (M/2 + H)+ Observ. | 1159 |
| Retention Time | 1.28 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Temperature | 40° C. |
| Column | Phenomenex LUNA C18, 30 × 2, 3u |

Biological Activity

The ability of the compounds of formula (I) to bind to PD-L1 was investigated using a PD-1/PD-L1 Homogenous Time-Resolved Fluorescence (HTRF) binding assay.

Homogenous Time-Resolved Fluorescence (HTRF) Binding Assay

The interaction of PD-1 and PD-L1 can be assessed using soluble, purified preparations of the extracellular domains of the two proteins. The PD-1 and PD-L1 protein extracellular domains were expressed as fusion proteins with detection tags, for PD-1, the tag was the Fc portion of Immunoglobulin (PD-1-Ig) and for PD-L1 it was the 6 histidine motif (PD-L1-His). All binding studies were performed in an HTRF assay buffer consisting of dPBS supplemented with 0.1% (with) bovine serum albumin and 0.05% (v/v) Tween-20. For the h/PD-L1-His binding assay, inhibitors were pre-incubated with PD-L1-His (10 nM final) for 15 m in 4 μl of assay buffer, followed by addition of PD-1-Ig (20 nM final) in 1 μl of assay buffer and further incubation for 15 m. HTRF detection was achieved using europium crypate-labeled anti-Ig (1 nM final) and allophycocyanin (APC) labeled anti-His (20 nM final). Antibodies were diluted in HTRF detection buffer and 5 μl was dispensed on top of the binding reaction. The reaction mixture was allowed to equilibrate for 30 minutes and the resulting signal (665 nm/620 nm ratio) was obtained using an EnVision fluorometer. Additional binding assays were established between the human proteins PD-1-Ig/PD-L2-His (20 & 5 nM, respectively) and CD80-His/PD-L1-Ig (100 & 10 nM, respectively).

Recombinant Proteins: Human PD-1 (25-167) with a C-terminal human Fc domain of immunoglobulin G (Ig) epitope tag [hPD-1 (25-167)-3S-IG] and human PD-L1 (18-239) with a C-terminal His epitope tag [hPD-L1(18-

239)-TVMV-His] were expressed in HEK293T cells and purified sequentially by ProteinA affinity chromatography and size exclusion chromatography. Human PD-L2-His and CD80-His was obtained through commercial sources.

Table 1 lists the $IC_{50}$ values for representative examples of this disclosure measured in the PD-1/PD-L1 Homogenous Time-Resolved Fluorescence (HTRF) binding assay.

TABLE 1

| Ex Number | HTRF $IC_{50}$ (μM) |
|---|---|
| 1001 | 0.0042 |
| 1002 | 0.0036 |
| 1003 | 0.016 |
| 1004 | 0.0043 |
| 1005 | 0.0014 |
| 1006 | 0.0028 |
| 1007 | 0.0016 |
| 1008 | n/a |
| 1009 | 0.0029 |

The compunds of formula (I) possess activity as inhibitors of the PD-1/PD-L1 interaction, and therefore, can be used in the treatment of diseases or deficiencies associated with the PD-1/PD-L1 interaction. Via inhibition of the PD-1/PD-L1 interaction, the compounds of the present disclosure can be employed to treat infectious diseases such as HIV, septic shock, Hepatitis A, B, C, or D and cancer.

It is to be appreciated that the Detailed Description section, and not the Summary and Abstract sections, is intended to be used to interpret the claims. The Summary and Abstract sections can set forth one or more but not all exemplary embodiments of the present disclosure as contemplated by the inventor(s), and thus, are not intended to limit the present disclosure and the appended claims in any way.

The present disclosure has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments, but should be defined only in accordance with the following claims and their equivalents.

What is claimed is:

1. A compound of formula (I)

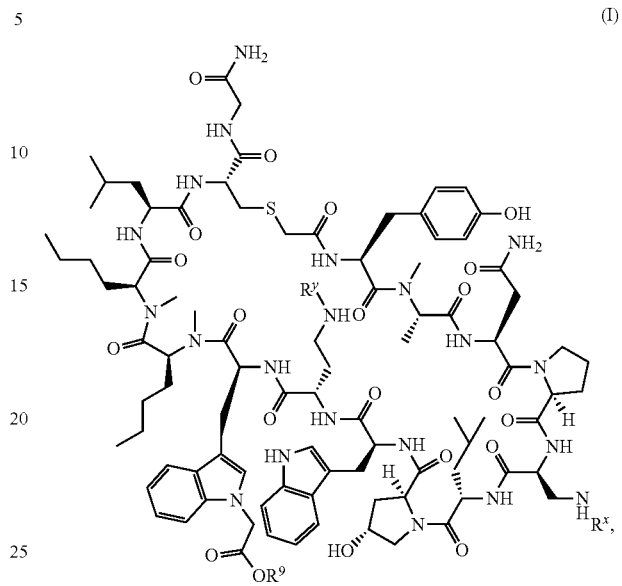

or a pharmaceutically acceptable salt thereof, wherein:
$R^x$ and $R^y$ are independently H,

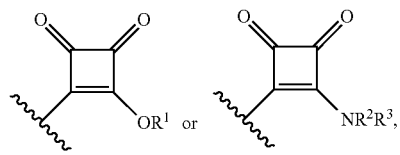

provided that at least one of $R^x$ and $R^y$ is other than H;
$R^1$ is H, halogen or $C_1$-$C_6$ alkyl;
$R^2$ and $R^3$ are independently H, halogen, $C_1$-$C_6$ alkyl, or aryl; said aryl group substituted with 0-3 $R^{3a}$,
$R^{3a}$ is halogen or $COOR^4$;
$R^4$ is H or $C_1$-$C_6$ alkyl; and
$R^9$ is H or $C_1$-$C_3$ alkyl.

2. The compound of claim 1 wherein
$R^2$ and $R^3$ are independently H, halogen, $C_1$-$C_6$ alkyl or phenyl; said phenyl group substituted with 0-3 $R^{3a}$,
$R^{3a}$ is halogen or $COOR^4$;
$R^4$ is H or $C_1$-$C_6$ alkyl; and
$R^9$ is H or $C_1$-$C_3$ alkyl.

3. The compound of claim 1, or a pharmaceutically acceptable salt thereof, wherein $R^x$ is H.

4. The compound of claim 1, or a pharmaceutically acceptable salt thereof, wherein $R^y$ is H.

5. The compound of claim 1, or a pharmaceutically acceptable salt thereof, wherein $R^9$ is H or —$CH_3$.

6. A pharmaceutical composition comprising a compound of claim 1, or a pharmaceutically acceptable salt thereof, and a pharmaceutically acceptable carrier.

7. A method of enhancing, stimulating, and/or increasing an immune response in a subject in need thereof, said method comprising administering to the subject a therapeutically effective amount of a compound of claim 1 or a pharmaceutically acceptable salt thereof.

8. A method of inhibiting growth, proliferation, or metastasis of cancer cells in a subject in need thereof, said method comprising administering to the subject a therapeutically effective amount of a compound of claim 1, or a pharmaceutically acceptable salt thereof.

9. The method of claim 8, wherein the cancer is selected from melanoma, renal cell carcinoma, squamous non-small cell lung cancer (NSCLC), non-squamous NSCLC, colorectal cancer, castration-resistant prostate cancer, ovarian cancer, gastric cancer, hepatocellular carcinoma, pancreatic carcinoma, squamous cell carcinoma of the head and neck, carcinomas of the esophagus, gastrointestinal tract and breast, and hematological malignancies.

10. A method of treating an infectious disease in a subject in need thereof, the method comprising administering to the subject a therapeutically effective amount of a compound of claim 1, or a pharmaceutically acceptable salt thereof.

11. The method of claim 10, wherein the infectious disease is caused by a virus.

12. A method of treating septic shock in a subject in need thereof, the method comprising administering to the subject a therapeutically effective amount of a compound of claim 1, or a pharmaceutically acceptable salt thereof.

13. A method for blocking the interaction of PD-L1 with PD-1 and/or CD80 in a subject, said method comprising administering to the subject a therapeutically effective amount of a compound of claim 1, or a pharmaceutically acceptable salt thereof.

* * * * *